United States Patent [19]

Miles

[11] 4,034,074

[45] July 5, 1977

[54] UNIVERSAL REAGENT 2-SITE IMMUNORADIOMETRIC ASSAY USING LABELLED ANTI (IgG)

[75] Inventor: Laughton E. M. Miles, Stanford, Calif.

[73] Assignee: The Board of Trustees of Leland Stanford Junior University, Stanford, Calif.

[22] Filed: Sept. 19, 1974

[21] Appl. No.: 507,347

[52] U.S. Cl. .............................. 424/1; 23/230 B; 424/1.5; 424/12

[51] Int. Cl.$^2$ .................. G01N 33/00; G21H 5/02; A61B 10/00

[58] Field of Search ............... 23/230 B; 424/1.5, 8, 424/12

[56] References Cited

UNITED STATES PATENTS 3,904,367   9/1975   Golibersuch .................. 23/230 B

OTHER PUBLICATIONS

Catt, Acta Endocrinologica Supplementum, No. 142, 1969, pp. 222–246.
Addison et al., Hormone and Metabolic Research, vol. 3, No. 1, Jan., 1971, pp. 59–60.
Midgley et al., Acta Endocrinologica Supplementum, No. 142, 1969, pp. 247–256.
Silman et al., Annual Review of Biochemistry, vol. 35, part II, 1966, pp. 873–880.
Miles et al., Nuclear Science Abstracts, vol. 30, No. 11, Dec. 15, 1974, abstract No. 29835.

*Primary Examiner*—Benjamin R. Padgett
*Assistant Examiner*—Christine M. Nucker
*Attorney, Agent, or Firm*—Robert G. Slick

[57] ABSTRACT

An improvement is made in 2-site immunoradiometric assay wherein a single labelled antibody can be used to assay many different antigens.

3 Claims, No Drawings

UNIVERSAL REAGENT 2-SITE IMMUNORADIOMETRIC ASSAY USING LABELLED ANTI (IgG)

The invention described herein was made in the course of work under a grant or award from the Department of Health, Education and Welfare.

SUMMARY OF THE INVENTION

The so-called 2-site IRMA (immunoradiometric assay) is a well established system for assays of antibodies and antigens and in general consists of an assay wherein an unknown antigen is insolubilized on the wall of a test tube or similar vessel. The usual method of insolubilizing the antigen is by reaction with solid-phase antibodies. An excess of a soluble radioactive labelled antibody is then placed in contact with the insolubilized anitgen to form an insoluble complex. The unreacted labelled material is washed away and the radioactivity of the complex remaining indicates the amount of the labelled material which has entered into the complex reaction and is therefore a measure of the amount of unknown antigen which is present.

One difficulty with such a system in the past is that it is necessary to prepare a purified specified radioactive antibody for each specific material which is to be analyzed. This is expensive and time consuming and also results in an unacceptable wastage of precious antisera.

In the course of the present invention a modification is made of the usual 2-site technique which permits a single readily-available and easily prepared labelled antibody to be used to assay many antigens. Thus, no labelled antigen or specific labelled antibody is required so that it is not necessary to prepare or maintain a stock or a large number of specific radioactive materials for testing a variety of materials. An easily-prepared radioactive labelled antibody to immunoglobulin (anti (IgG)) is employed for a large number of different analyses.

In accordance with a preferred embodiment of the invention, guinea pig anti (ferritin) is used as the antibody for the analysis of an unknown ferritin. Guinea pig anti (ferritin) formed as a coating on a tube and the unknown ferritin added (Reaction 1). One now adds an excess of a rabbit anti (ferritin) (Reaction 2). The labelled material is then added which is $^{125}I$ guinea pig anti (rabbit IgG) (Reaction 3). After the material is reacted, the excess of the radioactive material is washed out and the insoluble complex left behind is subjected to the usual gamma count. The readily available radioactive reagent could be employed for a variety of unknown materials.

Although the foregoing represents a summary of a preferred method of carrying out the invention, the general applicability can be shown by carrying out the mirror image reaction (Example 2). Thus, in Reaction 1 above, rabbit anti (ferritin) was employed while in Reaction 2 guinea pig anti (ferritin) was employed. The radioactive material for Reaction 3 was $^{125}I$ rabbit anti (guinea pig IgG). The general applicability is also demonstrated by application of the same labelled antibody to the measurement of two other antigens (Example 3).

IRMA is carried out by reacting the unknown antigen with specific soluble purified radioactive antibodies (Reaction 1). The radioactive complex remains in solution and unused radioactive antibodies are removed by reaction with a solid phase antigen (Ag-ImAd) (Reaction 2).

Use of specific labelled antibodies is avoided by using unlabelled, unpurified antibodies in Reaction 1, and undertaking an additional reaction (Reaction 3) in which the solid phase is reacted with labelled anti (IgG). The radioactivity bound into the solid phase will be inversely related to the amount of antigen originally present.

DESCRIPTION OF THE PREFERRED EMBODIMENT

The following examples illustrate preferred embodiments of the present invention:

EXAMPLE I

Antisera to purified human ferritin were prepared in two animal species (rabbits and guinea pigs). Anti (rabbit IgG) serum was prepared in guinea pigs. Guinea pig anti (ferritin) diluted 1:2000 was used to coat polystyrene tubes. $^{125}I$-anti (rabbit IgG) was prepared in the same way as previous radioactive antibodies as is known in the literature. Ferritin standards were made up in normal rabbit serum diluted 1:20 with 0.05 M veronal buffer pH 8.0, containing 4.5 gm/L NaCl, 200 mg/L sodium azide, 1 gm/l bovine serum albumin (hereafter referred to as BSA-buffer). Ferritin protein concentration was determined using the method of Lowry with bovine serum albumin standards.

The assay was carried out as follows: 0.2 ml of human ferritin standard was dispensed into the bottom of the antibody coated tube. The tubes were left at 4° C for 24 hours (Reaction 1), aspirated and washed once with BSA-buffer. 0.2 ml of rabbit anti (ferritin) diluted 1:2000 with BSA-buffer, was added and the tubes left at 4° C for a further 48 (Reaction 2). The tubes were then aspirated and washed twice with 0.04 M phosphate buffer pH 7.4, before adding 0.2 ml (20,000 cpm) of purified $^{125}I$-labelled guinea pig anti (rabbit IgG). The tubes were left at 4° C for 48 hours (Reaction 3), and then again aspirated, washed twice with the phosphate buffer to remove unbound labelled antibody and counted for 1 minute in an automatic gamma counter. As the concentration of antigen increases, the amount of radioactivity in the solid-phase increases. A standard curve was derived from quadruplicate determinations on ferritin standards containing 0, 0.33, 1.33, 5.31, 21.25, 85 and 340 ng of ferritin protein per ml. The data was analyzed using a version of the weighted, four-parameter logistic curvefitting method of Rodbard and Hutt, adapted for use on the IBM-360 and with 2-site IRMA.

The mean zero-dose radioactivity in this assay was 1772 cpm as compared with 2302 cpm for the lowest concentration of ferritin measured (0.33 ng/ml). The minimal detectable dose (two standard deviations from zero-dose) was 34 picograms and occurred when the tube radioactivity increased from 1772 to 2031 cpm (an increase from 7.7% to 8.83% of the total radioactivity added to the tube) (23,000 cpm). A 4.8 fold increase in tube radioactivity (2031 to 9781 cpm) was seen throughout the working range of the standard curve (0.17 to 50 ng/ml).

EXAMPLE II

In order to demonstrate the versatility of this system, a "mirror image" assay was established. In this assay the tubes were coated with rabbit-anti (ferritin); guinea-pig-anti (ferritin) was used in Reaction 2; and $^{125}I$-rabbit anti (guinea-pig IgG) was used in Reaction 3.

The results showed a good assay standard curve, but the zero-dose radioactivity is higher and the slope of the dose response curve not as steep as in Example 1, probably due to the lower affinity of the commercial anti (guinea-pig IgG).

EXAMPLE III

This example demonstrates the application of this same assay system (using the same labelled antibody) to the measurement of several different antigens. Antisera to glial fibraillary acidic protein (GFAP) and bovine parathyroid hormone (pThH) were prepared in both guinea pigs and rabbits. The assays were carried out as was done in the ferritin assay (Example I) with the guinea pig antiserum in the solid phase and the rabbit antiserum in Reaction 2. Reaction 1 was carried out using various concentrations of GFAP or pThH. Reaction 3 used the same preparation of $^{125}$I anti (rabbit IgG) used in Example 1 (total counts per minute = 45,000).

Results showed that in the GFAP assay 5829 cpm were bound into the solid phase in the absence of added GFAP, and the radioactivity increased steadily with increasing concentrations of added GFAP (11370 cpm at 1.1 μg/ml and 13470 cpm at 11 μg/ml). In the pThH assay 4224 cpm were bound into the solid phase at zero dose, and the radioactivity increased to 5565 cpm (7 μg crude extract/ml) and 7601 (70 μg/ml).

I claim:

1. The process of making an immunoradiometric quantitative assay of an unknown quantity of a known antigen of a first animal species comprising the steps of:
   a. preparing an antibody to the antigen of the first animal species in a second animal species,
   b. causing said antibody to be bound to a reaction site,
   c. reacting and binding said known antigen with said bound antibody,
   d. preparing an antibody to said known antigen in a third animal species and reacting and binding the same with the bound known antigen of paragraph c,
   e. preparing a purified, radioactive labeled antibody to the immunoglobulin of said third animal species in said second animal species and reacting and binding the same with the bound material of paragraph d,
   f. removing unreacted material from said reaction site, and
   g. measuring the radioactivity of the bound material to determine the quantity of the known antigen.

2. The process of claim 1 wherein the known antigen is human, the second animal is guinea pig and the third animal is rabbit.

3. The process of claim 1 wherein the known antigen is human, the second animal is rabbit, and the third animal is guinea pig.

* * * * *